United States Patent [19]
Dougherty

[11] Patent Number: 5,454,912
[45] Date of Patent: Oct. 3, 1995

[54] SUSPENSION QUALITY MONITORING APPARATUS

[76] Inventor: Steven J. Dougherty, 18310 17th St. East, Sumner, Wash. 98390

[21] Appl. No.: 951,282

[22] Filed: Sep. 25, 1992

[51] Int. Cl.[6] .................................................. G01N 1/10
[52] U.S. Cl. ...................... 162/263; 73/53.03; 73/64.56; 73/863.81
[58] Field of Search .................. 162/49, 198, 263, 162/238; 73/53.01, 53.03, 37, 64.56, 863, 863.81, 864.12; 422/63, 81; 356/404, 410, 239; 250/437, 438

[56] References Cited

U.S. PATENT DOCUMENTS

| | | | |
|---|---|---|---|
| 3,201,993 | 8/1965 | Moody et al. | |
| 3,461,030 | 8/1969 | Keyes | |
| 3,498,719 | 3/1970 | Wing et al. | |
| 3,604,814 | 9/1971 | Skeggs | 356/410 |
| 3,614,452 | 10/1971 | Felton | 356/410 |
| 3,709,614 | 1/1973 | Hayakawa | 356/208 |
| 3,709,615 | 1/1973 | Blakeslee et al. | 356/224 |
| 3,954,341 | 5/1976 | Uffenheimer | 356/410 |
| 4,184,204 | 1/1980 | Flohr | 364/471 |
| 4,225,385 | 9/1980 | Hughes, Jr. et al. | 162/263 |
| 4,276,119 | 6/1981 | Karnis et al. | 162/49 |
| 4,318,180 | 3/1982 | Lundqvist et al. | 364/555 |
| 4,342,618 | 8/1982 | Karnis et al. | 162/49 |
| 4,374,703 | 2/1983 | Lebeau et al. | 162/253 |
| 4,402,604 | 9/1983 | Nash | 356/237 |
| 4,409,853 | 10/1983 | Chase et al. | 73/863 |
| 4,415,408 | 11/1983 | Greey | 162/198 |
| 4,441,960 | 4/1984 | Karnis et al. | 162/49 |
| 4,504,016 | 3/1985 | Wikdahl | 241/24 |
| 4,514,257 | 4/1985 | Karlsson et al. | 162/49 |
| 4,590,165 | 5/1986 | Gilles et al. | 436/49 |
| 4,758,308 | 7/1988 | Carr | 162/263 |

*Primary Examiner*—Geoffrey L. Knable
*Attorney, Agent, or Firm*—Robert W. Beach

[57] ABSTRACT

A sample of slurry is withdrawn continuously from a pressure pipe through which the slurry flows by a diluting sample-extractor mounted on the pipe. Dilution water is added continuously to the extractor to mix with the withdrawn sample to provide dilute slurry, and the quality of the dilute slurry is evaluated by passing it through a viewing window chamber and taking periodic photographs of the dilute slurry passing through such viewing window chamber.

4 Claims, 6 Drawing Sheets

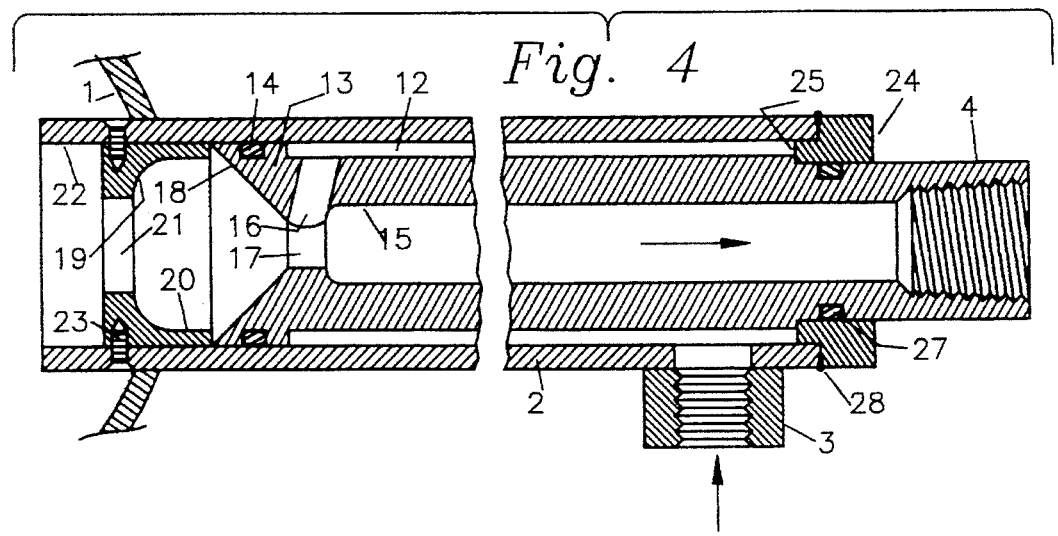
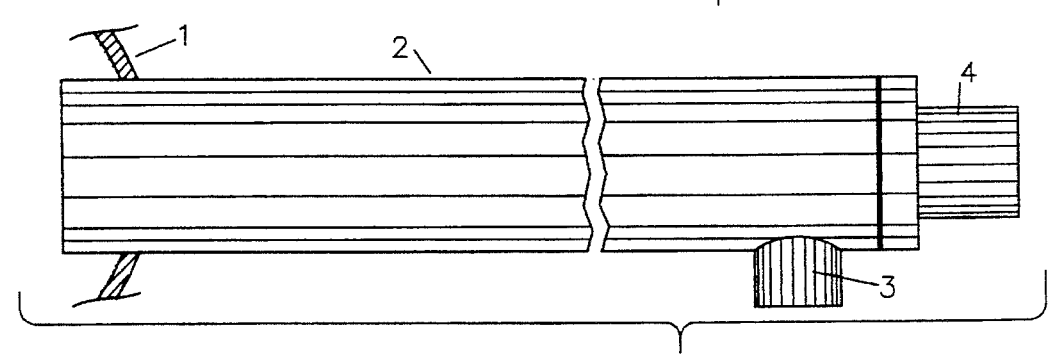
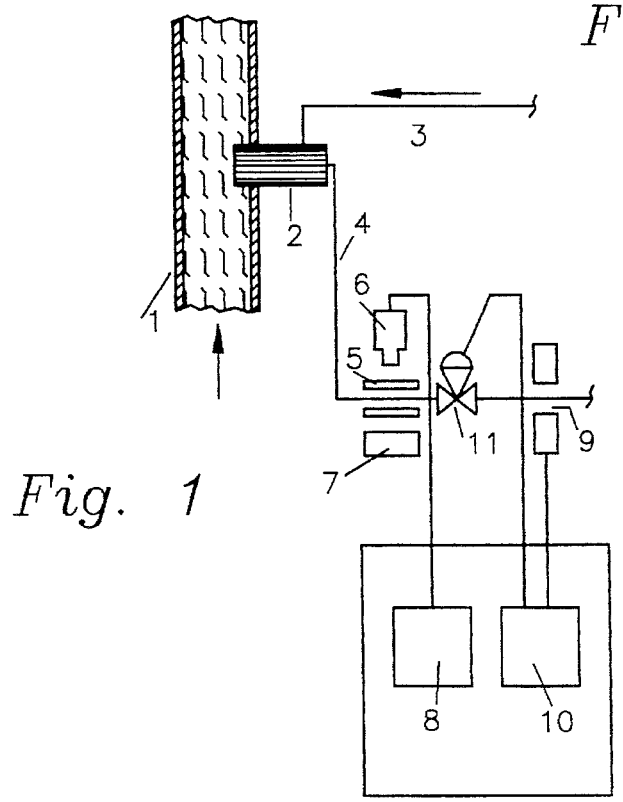
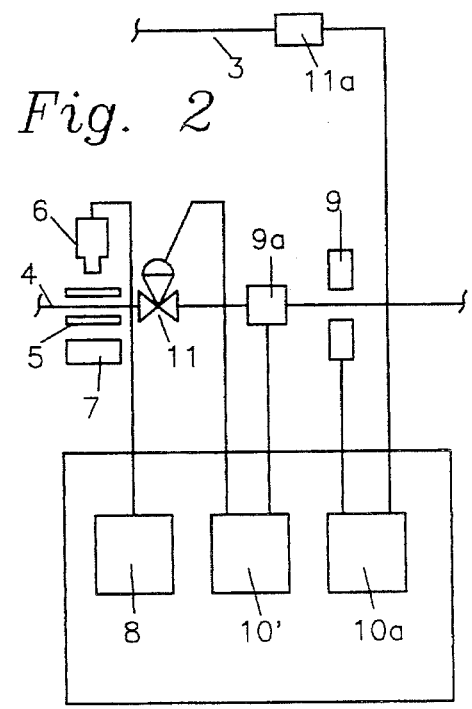

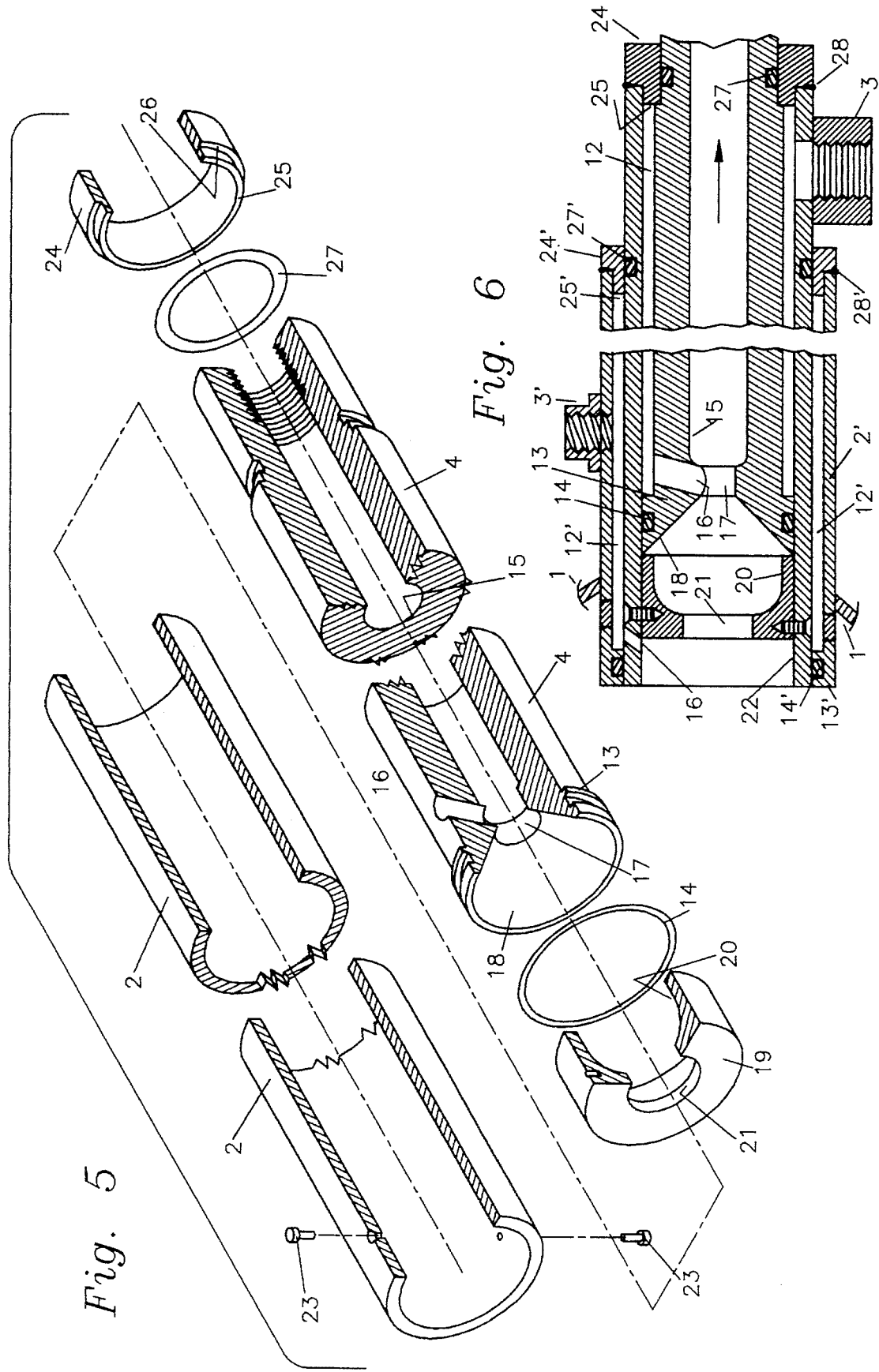

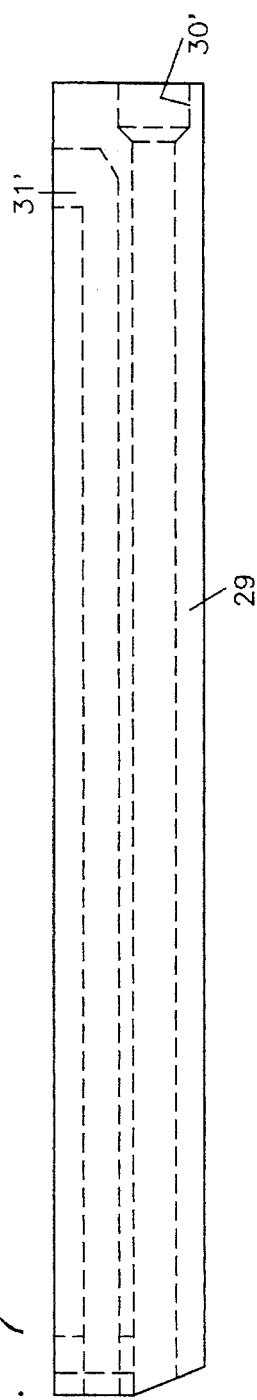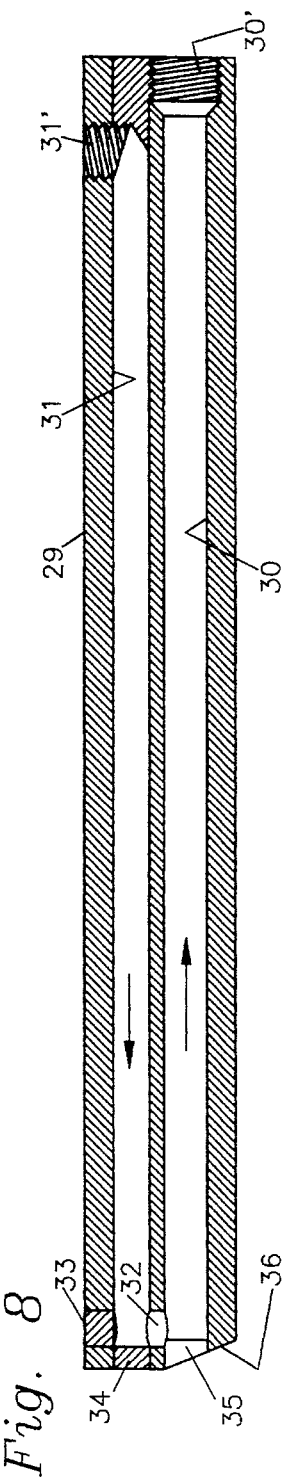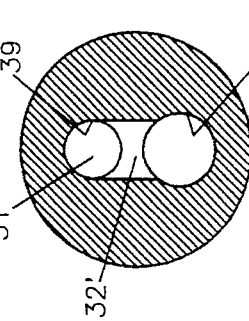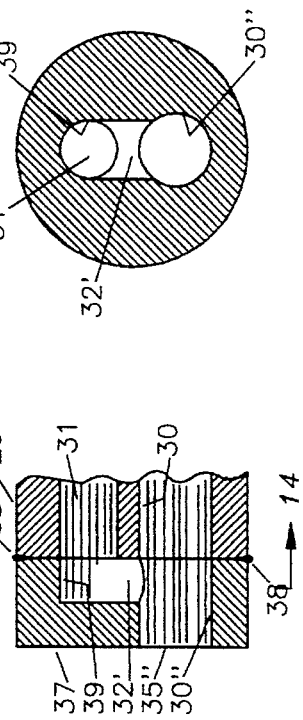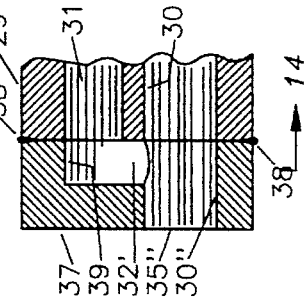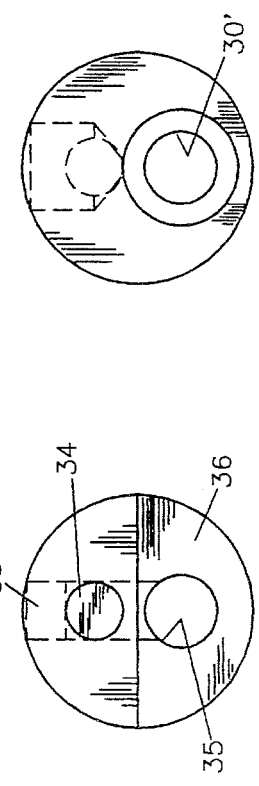

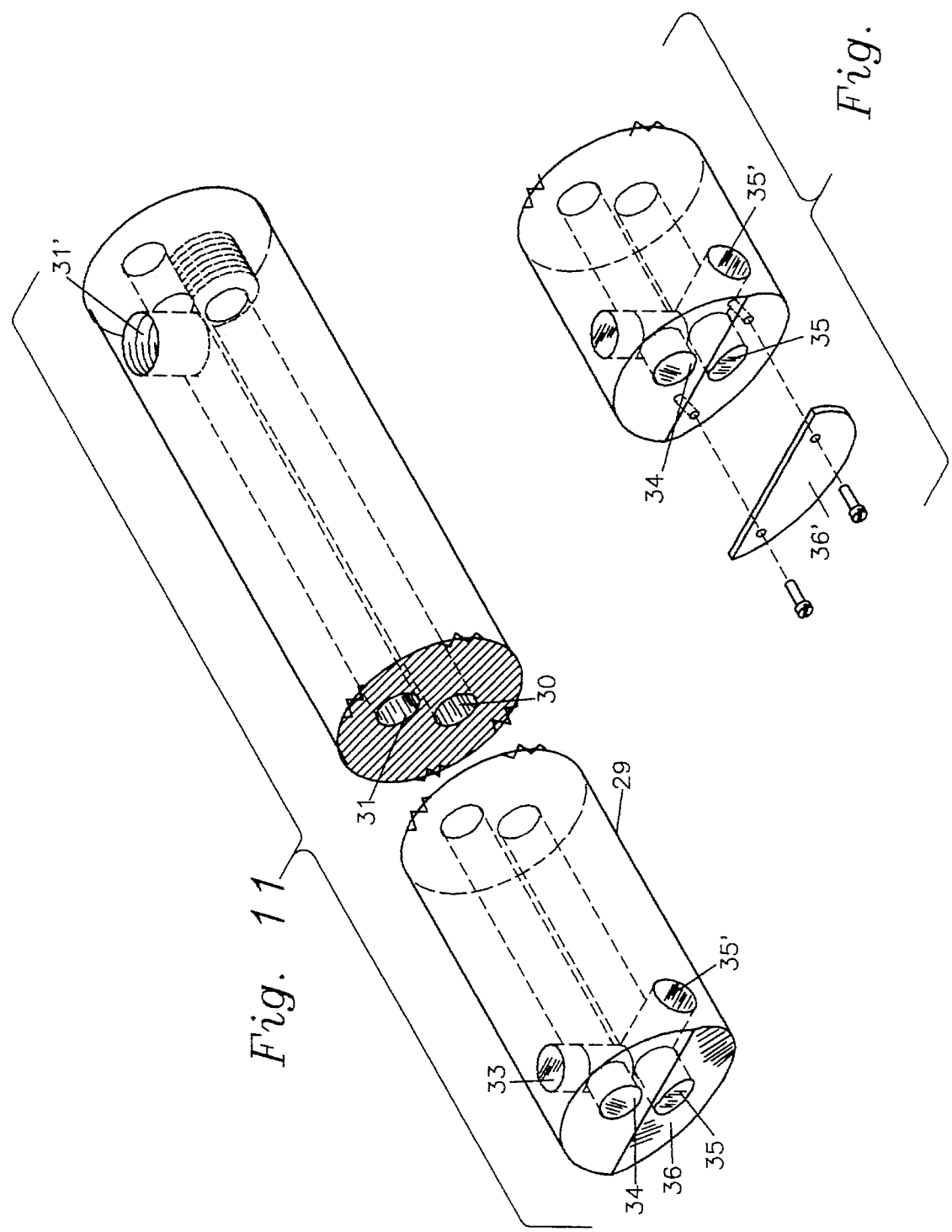

SUSPENSION QUALITY MONITORING APPARATUS

BACKGROUND OF THE INVENTION

1. Field of the Invention

This invention relates to apparatus and a process for monitoring the quality of a suspension such as a slurry. Such monitoring may be for the purpose of determining the purity of the slurry, that is, the presence of foreign or adulterating particulate material and/or for determining the uniformity or constancy of the consistency of the slurry.

2. Prior Art

U.S. Pat. No. 4,758,308, issued Jul. 19, 1988, to Carr refers at column 2, lines 32 to 35 to a paper entitled "Detection and Quantification of Sticky Contaminants and Recycled Fiber Systems" by Doshi, Dyer and Krueger, stating at column 2, lines 52 to 58 that:

> . . . the sample of the pulp either directly or after concentration of the contaminants in a sample is formed into a hand sheet and allowed to dry for handling. The air dryed hand sheet is placed between appropriate filter paper and hot pressed to form a sheet in which the contaminants can be monitored.

The Carr patent also discusses prior patents at column 1, lines 33 to 62 as follows:

> The patent art discloses photodetection monitoring means for particles detection of pulp. For example, U.S. Pat. Nos. 4,402,604 which issued Sep. 6, 1983 and 4,225,385 which issued Sep. 30 1980 disclose withdrawing of a sample of the pulp stock passing of the sample through a photoelectric detection system which detects the presence of dirt, shives and the like. U.S. Pat. No. 4,402,604 which issued Sep. 6, 1983 discloses a system whereby the liquid pulp or the pulp to be inspected is passed in a liquid state between a pair of transfer plates. The pulp is mixed with a pure liquid, that is, one without fiber content to control the consistency of the mixture as it passes through the plates. Light sources are applied to opposite sides of the moving sheet and a plurality of photosensitive devices are located in a row across the pipe to receive both reflected light and transmitted light. A series of photoelectric diodes are mounted across the plate to continuously scan the moving pulp. The output of each device is a signal dependent on the intensity of the light, and therefore the presence or absence of the particles. U.S. Pat. No. 4,225,385 discloses a method for directly passing of the pulp through a mixing unit for dilution of water and then through a inspection tube having a photoelectric device to scan the liquid as it passes through. Other patents have further considered analysis of the virgin pulp for foreign matter; for example, U.S. Pat. Nos. 4,184,204, 3,709,615, 4,318,180, 4,276,119, 4,441,960.

Additional United States patents cited by the U.S. Patent and Trademark Office against the Carr application resulting in U.S. Pat. No. 4,758,308 include U.S. Pat. Nos. 4,342,618, 4,374,703, 4,504,016 and 4,514,257.

SUMMARY OF THE INVENTION

The monitoring apparatus and process of the present invention operates continuously and can be used for evaluating the quality of various kinds of slurries, but it is particularly useful for evaluating the quality of paper pulp slurry.

A principal object of the invention is to provide apparatus and a process for sampling slurry from a pressure pipe by extracting a small but representative portion of the slurry flow on a continuing basis and to dilute it substantially at the point of extraction.

A further object of the invention is to provide a periodic photographic record of the dilute slurry automatically.

It is also an object to evaluate the quality of the dilute slurry, including determining the amount and character of adulterant material in the slurry and, if desired, the consistency of the dilute slurry.

Another object is to control the consistency to which the sample withdrawn from the pressure pipe is diluted by regulating the flow through the outflow duct automatically in response to the consistency of the dilute slurry.

It is also an object to mix dilution water with slurry to provide a uniform blend.

A further object is to provide apparatus which is of simple construction, is compact and which operates effectively.

The foregoing objects can be accomplished by supplying dilution water into an outflow duct from a pressure pipe carrying slurry at a location adjacent to a sampling port in such pressure pipe and conveying the diluted slurry continuously to evaluating mechanism which includes photographing mechanism and consistency-determining mechanism.

BRIEF DESCRIPTION OF THE DRAWINGS

FIG. 1 is a circuit diagram of one type of monitoring apparatus of the present invention; and FIG. 2 is a circuit diagram of another type of monitoring apparatus of the present invention.

FIG. 3 is a side elevation of, and FIG. 4 is a longitudinal section through, a slurry sample-extracting device usable in the apparatus shown in FIG. 1 or FIG. 2.

FIG. 5 is a top perspective of the sample-extracting device shown in FIGS. 3 and 4 with parts shown in exploded relationship and with parts broken away.

FIG. 6 is a longitudinal section through an alternative type of sample-extracting device usable in the apparatus shown in FIG. 1 or FIG. 2.

FIG. 7 is a side elevation of, and FIG. 8 is a longitudinal section through, a further alterative type of sample-extracting device usable in the apparatus shown in FIG. 1 or FIG. 2.

FIG. 9 is an end elevation seen from the left end of the device shown in FIGS. 7 and 8 intended for projection into a pressure pipe carrying slurry; and FIG. 10 is an end elevation of the opposite end of such device.

FIG. 11 is a top perspective of the device shown in FIGS. 7 and 8; and FIG. 12, is a fragmentary top perspective of an end portion of such device with parts in exploded relationship.

FIG. 13 is a fragmentary longitudinal vertical section through the end portion of a sample-extracting device to be inserted through the wall of a pressure pipe carrying slurry which is a modification of the device shown in FIGS. 7 and 8; and FIG. 14 is a transverse section through the device of FIG. 13 taken along line 14—14 of that figure.

DETAILED DESCRIPTION

Figure 15:
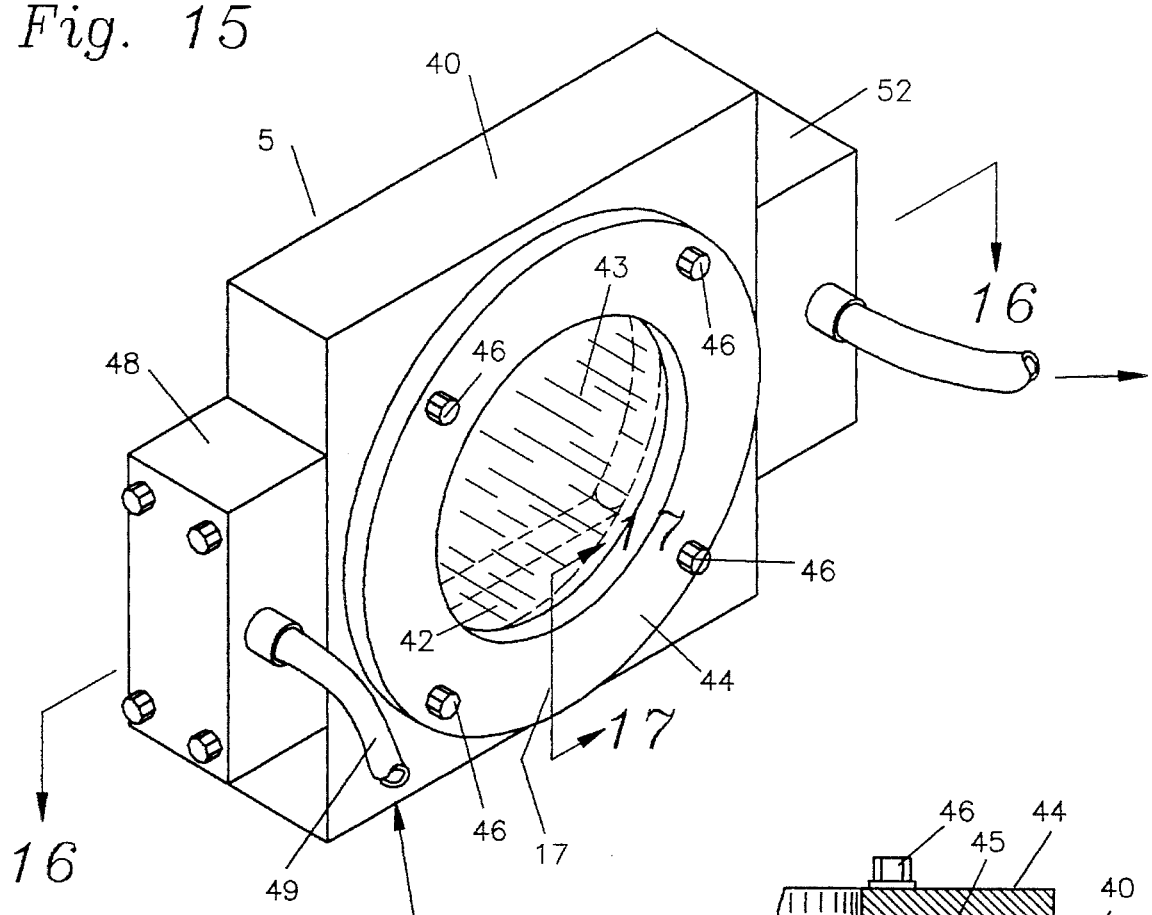
FIG. 15 is a top perspective of a viewing chamber usable in the apparatus shown in FIG. 1 or FIG. 2.

The purpose of the present apparatus and process is to monitor the character and quality of slurry flowing through the pressure pipe 1 on a substantially continuous basis. Such slurry may be watery pulp or other dilute fluid suspension. Such slurry flows through the pipe 1 in the direction indicated by the arrow in FIG. 1 and may have a consistency of 0.3 percent to 15.0 percent of solids by weight. Pulp supplied to some paper-making machine headboxes, for example, may have a consistency as low as 0.3 percent of solids.

In order to be able to identify and evaluate impurities such as dirt, sand, knots, lumps, shives, ink particles, plastics and metal staples in the pulp, it is necessary to dilute the pulp slurry considerably, usually with water although in some instances other types of diluents may be used, such as from a consistency of 0.3 percent to 15 percent of solids to liquid by weight down to 100 to 3000 parts per million of solids to liquid by weight, which represents a dilution of up to 1,500 to 1, preferably, approximately 500 parts per million. It is desired that such diluting be effected on a continuous basis by a diluting sample-extractor.

A diluting sample-extractor 2 is shown in FIG. 1 and FIG. 2 as a cylindrical pipe mounted on the pressure slurry pipe 1 having its sample entrance end inserted through an aperture in the wall of the pressure slurry pipe. The pipe 1 may be from two inches to 36 inches in diameter, for example. Such sample-extractor 2 is located in a branch from the slurry pipe. Preferably the sample extractor is inserted into such branch through a sleeve including a ported valve body in a valve which can be closed to stop flow through the branch when the sample-extractor is removed. Such installation enables the sample-extractor to be installed and removed quickly and conveniently. The maximum diameter of the diluting sample-extractor may be approximately two inches, and the sample entrance end of the extractor may project into the pressure pipe 1 approximately one inch.

Diluent, usually water, is supplied to the diluting sample-extractor through a dilution water supply conduit 3. The diluted slurry flows out of the extractor continuously through an outflow duct pipe 4 which is connected to a viewing window chamber 5. During passage of the diluted slurry through the viewing chamber, periodic photographs of the dilute slurry may be taken by a camera 6 while the viewing chamber is illuminated by a light source 7, preferably of the light-emitting diode (LED) type, located at the side of the viewing chamber opposite the camera 6 as shown in FIG. 1.

The purpose of taking periodic photographs is to evaluate the amount of foreign material such as dirt, sand, knots, lumps, shives, plastic and metal staples that may be carried by the pulp. The camera may be connected to an imaging analyzer 8 which will automatically analyze each photograph taken to evaluate the content of foreign matter shown in such photograph. The designation "photograph" is used in this description in a generic sense to indicate exposure of any photosensitive medium to provide pictures or data indicative of the presence and amount of such foreign material.

From the viewing window chamber 5, the dilute slurry sample flows to a consistency meter 9, shown in FIG. 1 as being connected to a consistency analyzer 10 which monitors changes in consistency. Such consistency analyzer is connected to an automatic outflow throttling valve 11 that is actuated automatically in response to variations in the consistency of the dilute slurry passing through the consistency meter 9 to alter the area of the outflow passage through the valve 11. Such control can maintain the consistency of the dilute sample within predetermined limits because the quantity of dilution water supplied by conduit 3 is constant. Maintaining the consistency between such limits enhances the ability of the camera 6 to detect foreign material in the slurry. The consistency information can be used to correlate the amount of foreign material with the total amount of solid material in the slurry.

In the apparatus shown in FIG. 2, the setting of the outflow throttling valve 11 is under the control of a flow meter 9a located in the outflow duct 4 and connected to the throttling valve 11 through control mechanism 10'. With such control apparatus, the valve 11 is adjusted to maintain the flow through the outflow duct pipe 4 and evaluating apparatus constant independent of the consistency of the dilute slurry. In this instance, the consistency meter 9 is connected to a consistency analyzer 10a which also is connected to a control valve 11a in the dilution water supply conduit 3 for the purpose of regulating such water supply to dilute the slurry sample to a predetermined consistency.

The throttling valve 11 will also maintain the dilute slurry between the extractor 2 and the throttling valve under pressure sufficient to keep any gas content of the slurry in solution so that bubbles will not be present in the dilute slurry flowing through the viewing chamber 5 which would obscure or interfere with the evaluation of foreign solid matter in the dilute slurry by the photographing procedure of the camera 6 and the imaging analyzer 8.

In the form of diluting sample extractor shown in FIGS. 3, 4 and 5, the outflow duct 4 is located concentrically in the sample-extractor 2 spaced from its outer wall to provide an annular dilution water supply conduit 12 into which dilution water is supplied by the pipe 3 as shown in FIG. 4, so that the outer wall of the outflow duct 15 forms a common wall between the dilution water supply conduit 12 and the outflow duct. The inner end of the outflow duct has a head 13 located adjacent to the sample-entering end of the extractor, and such head has a sealing O-ring 14 received in an annular groove in the head to provide a seal closing the end of the annular dilution water passage adjacent to the sample inflow end of the extractor.

The closed end of the annular dilution water passage 12 is connected to a central outflow duct passage 15 through the extractor by one or more crossfeed ports 16 extending generally radially through the wall of the outflow duct adjacent to the sample entrance end of the extractor projected into the pressure pipe 1 so that the outflow duct passage 15 forms a blending or mixing chamber. Preferably the outflow duct 15 has a constriction 17 at its entrance into which the crossfeed port or ports 16 connects. Such constriction is preferably 3/8 inch to 1/2 inch in diameter, which would block flow of larger chunks of foreign matter into the outflow duct passage 15. As shown in FIG. 4, the extent of the crossfeed port 16 circumferentially of the constriction 17 is a minor portion of the circumference of such construction and of the outflow duct 15 so as to produce an inflow stream of diluent.

Immediately upstream from the dilution water inflow port or ports 16 and constriction 17 is a high-pressure enlargement mixing chamber connected to the constriction 17 of the outflow passage by a frustoconical funnel 18. Such mixing chamber is formed by the cavity 20 within insert 19, which cavity has a large end communicating with the funnel 18 and a smaller sample entrance port or sampling port 21 through the wall of the insert adjacent to the end of the extractor projecting into the pressure pipe 1. The sampling port 21 is considerably larger than the constriction 17, having a diameter approximately twice as great as the diameter of the constriction. The maximum diameter of the mixing chamber formed by the funnel 18 and the cavity 20 in the insert 19 is approximately twice as great as the diameter of the sampling port 21. The combined extent of the funnel and insert cavity lengthwise of the extractor is approximately equal to the maximum diameter of the mixing chamber. Because the cross-sectional area of the mixing chamber transversely of the direction of extracted pulp slurry flow through it is larger than the area of the sampling port 21 and the outflow duct downstream from such chamber the velocity of flow through the mixing chamber will be decreased. Projection of the dilution water through the port 16 directed toward the mixing chamber in a direction transversely of the direction of the flow of extracted pulp slurry through the mixing chamber, produces turbulence in such chamber to promote blending of the dilution water with sample slurry flowing into the mixing chamber through the sampling port 21 from the pressure pipe 1.

The insert 19 fits snugly within the bore of the extractor 2 at a location spaced lengthwise inward from the end of the extractor projecting into the pressure pipe 1 to form a flange 22 which may be annular encircling the sampling port 21. The insert can be held in place by securing screws 23 extending radially through the wall of the extractor into the outer wall of the insert 19.

The end of the annular passage 12 remote from the pressure pipe 1 is closed by a collar 24 closely encircling the external periphery of the outflow duct 4 and having an internal annular flange 25 of a size to fit closely within the adjacent end of the outer pipe of the extractor 2. A seal between such collar 24 and the exterior of the outflow duct tube is effected by an O-ring 27 received in an annular groove formed in the outer wall of the outflow duct and contacting the inner periphery of the collar 24. Such collar is secured to the adjacent end of the outer pipe of the extractor 2 by an annular weld 28.

In operation, the pressure of the slurry flowing through the pressure pipe 1 is exerted on the portion of the slurry next to the sample entrance port 21 of the extractor so that sampling flow of the slurry will occur continually from the pressure pipe 1 into the sample entrance 21. As soon as the sample flow of slurry enters the mixing chamber enlargement of the flow passage, such slurry will be blended with the flow of dilution water entering through the crossfeed port or ports 16 into constriction 17 to dilute the slurry sample as stated above.

The size and shape of the enlarged chamber 20 in the insert 19, the size of the constriction 17 and the size of the crossfeed port or ports 16 can be selected to accomplish an effective blending of the dilution water with the sampling flow so that the outflow through outflow duct passage 15 will be diluted to the desired consistency to enable proper evaluation of the slurry by photographing and consistency metering. The amount of slurry sample obtained, and the consistency to which the sample is diluted, are determined by the flow rate of dilution water into the extractor through port 3 and the flow rate of diluted sample out of port 4 of the extractor. These flows are controlled as described above.

If greater dilution of the slurry sample is desired, it may be necessary in order to obtain uniform dilution to provide a supply of dilution water in addition to that supplied through connection 3 to the sample-extractor 2 shown in FIGS. 3, 4 and 5. Such additional dilution water can be supplied to the sample-extractor 2' shown in FIG. 6. The construction of this sample-extractor is generally the same as the sample-extractor shown in FIGS. 3, 4 and 5 but, in this instance, the sample-extractor has an additional casing 2' concentric with the central outflow duct passage 15 through the extractor and spaced outwardly from the wall forming the annular dilution water supply conduit 12 to provide an additional annular supply conduit 12' to which dilution water can be supplied through a connection 3'.

The end of the outer tube is sealed to the intermediate tube of the extractor by a collar 24' sealed to the intermediate tube of the extractor by an O-ring 27' and connected to the outer tube of the extractor by an annular weld 28'.

The end of the annular passage 12' is connected to the recess formed by flange 22 encircling the sample entrance 21 by one or more supplemental dilution water ports 16'. With such a sample-extractor, dilution water can be supplied through port or ports 16' to effect an initial dilution of the slurry sample entering the port 21, and this slurry sample can then be diluted further by dilution water supplied by port or ports 16 to the constriction 17 and to the mixing chamber between such constriction and the sampling port 21.

The alternative type of diluting sample-extractor 29 shown in FIGS. 7 to 11 again is preferably of cylindrical shape having parallel side-by-side passages extending through it separated by a common wall including an outflow duct passage 30 having an internally threaded port 30' at the end remote from the end to be inserted into the pressure pipe 1 for connection to the outflow duct pipe 4. The extractor also has extending through it the dilution water supply conduit 31 which is parallel to the passage 30 and has an internally threaded port 31' for connection to the dilution water supply conduit 3.

The common wall separating the passages or bores 30 and 31 has a crossfeed port 32 through it adjacent to the end of the extractor to be inserted into the pressure pipe 1 and essentially at the upstream end of the outflow duct passage 30. Because the extractor 29 is of integral structure, the crossfeed port 32 is drilled by drilling through the outer wall of the extractor for passage of the drill through the dilution water passage 31 into the partition between the two passages 30 and 31. The hole drilled through the outer wall of the extractor is then closed by a tight plug 33. The bore 31 may be drilled from the end of the extractor to be inserted into the pressure pipe 1 and, after such drilling has .been completed, the end of the bore can be closed by a tight plug 34.

The sample entrance port or sampling port 35 is formed by the end of the outflow bore 30 opening at the end of the extractor to be inserted into the pressure pipe 1. Passage 30 forms a mixing chamber for blending the dilution water with the slurry sample entering port 35.

As shown in FIGS. 7, 8 and 9, the end portion of the extractor 29 may be beveled to provide a bevel or incline 36 for the end of the extractor inserted into the slurry pressure pipe which incline is at an angle relative to the direction of flow of slurry toward it through the pressure pipe, to reduce the tendency for the particulate material in the slurry in pressure pipe 1 to stratify as it turns from the flow direction in pipe 1 into the sampling port 35. While such bevel 36 may extend over the entire end of the extractor, it is preferably of substantially semicircular shape extending over only that portion of the extractor end through which the sampling port 35 opens. Such bevel 36 also increases the pressure for extraction of sampling flow from the flow of slurry through the pressure pipe 1 because the bevel faces upstream relative to the flow of slurry through the pressure pipe and therefore produces a component of the dynamic flow pressure toward the sampling port 35.

The operation of the apparatus using a diluting sample-extractor 29 of the type shown in FIGS. 7 to 11 is generally the same as described in connection with the extractor shown in FIGS. 3 to 5. The component of dynamic pressure or velocity pressure in pipe 1 in addition to static pressure exerted on the sample flow entering the entrance port 35 resulting from bevel 36 deters escape into pipe 1 of dilution water entering the outflow duct passage 30 through the crossfeed port 32. Instead, such dilution water blends with and dilutes the sampling flow as the combined flow travels to the right as seen in FIG. 7 through the outflow duct bore 30 to the connection 30' for the outflow duct pipe 4. Again, the sampling flow of slurry extracted from the pressure pipe 1 is immediately diluted continuously to produce a dilute slurry for evaluation in the viewing chamber 5 and the consistency meter 9.

Depending on the pressure in the pressure pipe 1 and the type of slurry flowing through it, it may be desirable to modify the type of extractor shown in FIGS. 7 to 11 by covering the end bevel 36 with a plate 36' as shown in FIG. 12 to close the sample entrance port 35. In lieu of such port, a radial port 35' can be drilled through the side of the extractor 29 as shown in FIG. 11 and FIG. 12 to communicate with the portion of the outflow passage 30 adjacent to the end of the extractor inserted into the pressure pipe 1. By turning the extractor 29 about its longitudinal axis, the radial port 35' can be directed relative to the direction of flow of slurry through the pressure pipe 1 either upstream or downstream or in any intermediate position between upstream and downstream to obtain the desired inflow pressure from the pressure pipe 1 to the outflow duct passage 30.

A further modification of the diluting sample extractor 29 of FIGS. 7 and 8 is shown in FIGS. 13 and 14 in which the dilution water passage 31 is connected to the outflow passage 30 by a crossfeed port recess 32' formed in an end cap 37 for the end of the diluting sample-extractor 29 to be inserted into the pressure pipe 1 instead of drilling through the wall of the dilution water passage into the partition between the dilution water passage and the outflow passage as described in connection with the extractor shown in FIGS. 7 to 9. Such end cap closes the end of the dilution water passage 31 except for such crossfeed port.

The extractor end cap 37 shown in FIGS. 13 and 14 has a duct 30" through it in continuation of outflow passage 30 and of the same size and location to provide the sample entrance port 35". The end of the cap 37 next to the extractor 29 then has a recess 39 in registration with and forming a continuation of the dilution water passage 31. The recess 39 has a portion forming a crossfeed port 32' connecting with a side of the duct 30". Slurry sample can enter the port 35" from the pressure pipe 1, be diluted in duct 30" by dilution water supplied through the passage 31 and the recess 39 including crossfeed port 32' in cap 37 to flow through the outflow duct and 30 to the connection 30' for the outflow duct 4. The cap 37 is secured to the end of the extractor 29 by an annular weld 38. Part or all of the end of the cap 37 remote from the body of the extractor could have a bevel to include the sampling port 35" corresponding to the bevel 36 shown in FIGS. 7, 8, 9 and 11.

The viewing window chamber 5 to which the outflow duct 4 is connected as shown in FIG. 1 and FIG. 2 is shown in detail in FIGS. 15 to 18. Such chamber includes a frame 40 which may be square and has generally circular openings 41 in its opposite sides. Within such openings the frame has circular segment partitions 42 projecting oppositely into the central opening through the frame to provide ledges on which thick circular transparent glass or plastic windows 43 may seat. Such windows are held in place by retaining rings 44 sealed to the window by O-rings 45 fitting against the margins of the openings 41 in frame 40, the edge of the window adjacent to its outer surface and the retaining ring 44. The outer peripheral corner of each window may be chamfered to provide a beveled seat engageable by the sealing O-ring.

Figure 17:
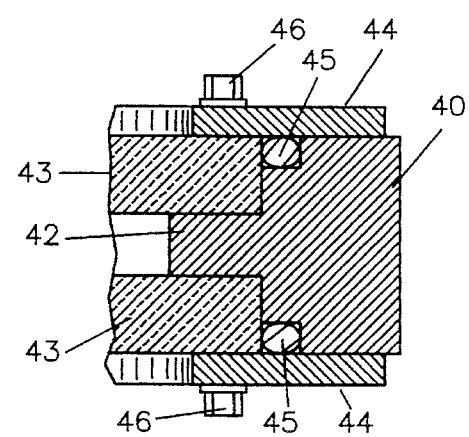
FIG. 17 is a fragmentary enlarged detail section through a portion of the viewing chamber shown in FIGS. 15 and 16 taken along line 17—17 of FIG. 15.
Figure 16:
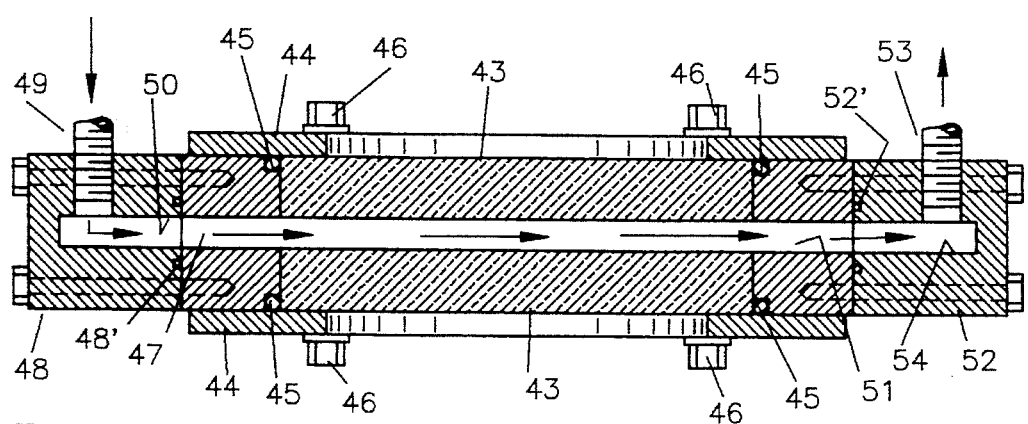
FIG. 16 is a section through such chamber taken along line 16—16 of FIG. 15.
Figure 18:
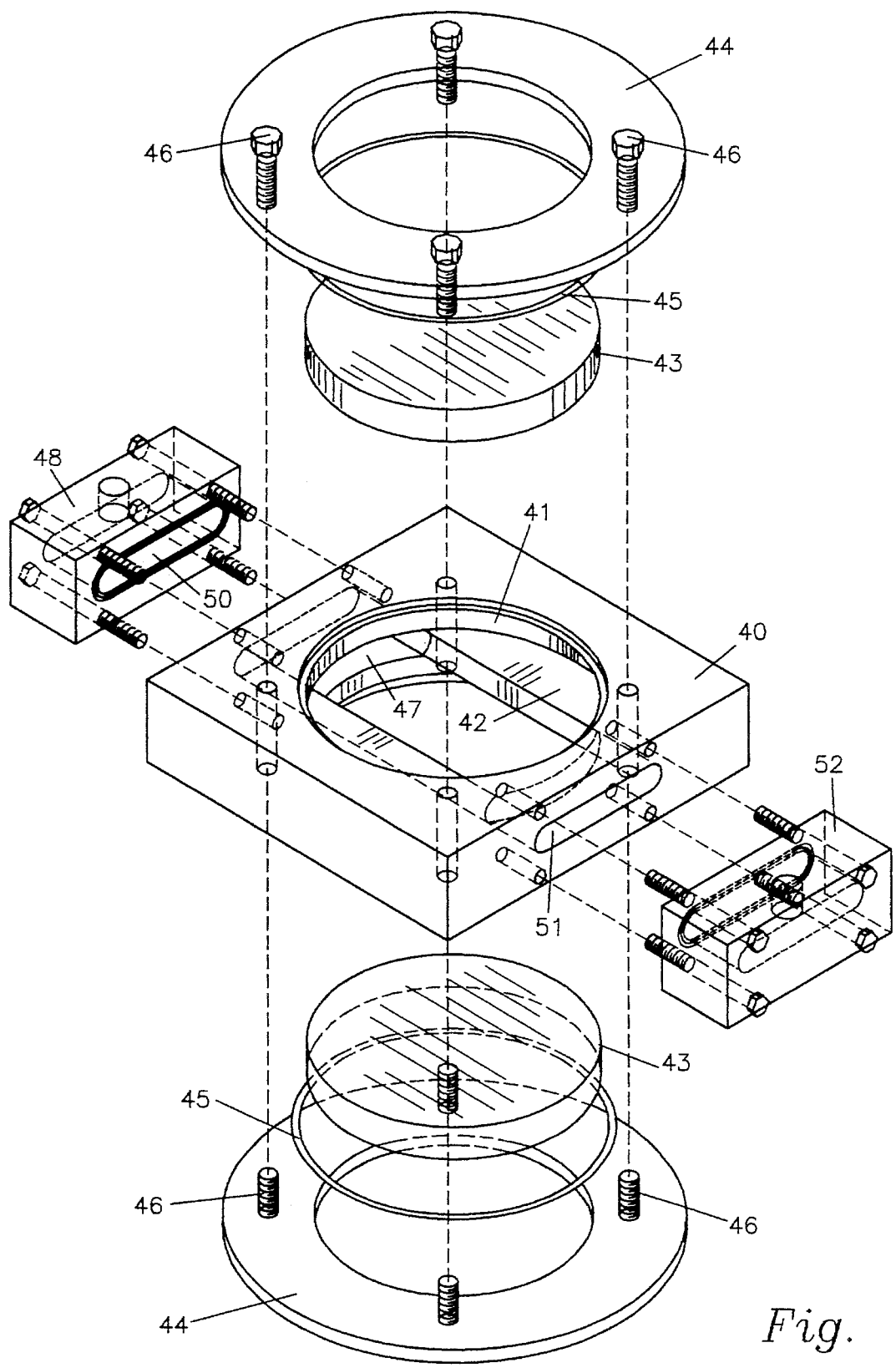
FIG. 18 is a top perspective of the viewing chamber shown in FIG. 15 with parts in exploded relationship.

The retaining rings 44 are of a width to extend a considerable distance radially inward from their peripheries to overlap the margins of the windows 43 as shown in FIGS. 16 and 17. The retaining rings are secured in place by bolts 46 spaced circumferentially of the rings, extending through holes in such rings and threaded into tapped holes in the frame 40.

The viewing chamber between the two windows 43 and between the partitions 42 is supplied with dilute slurry through an inlet transition slot 47 in the frame 40 adjacent to an inlet connecting block 48 bolted to the rim of the frame. An O-ring 48' seals the joint between the block and the frame 40. A nipple 49 is connected to a passage in such block leading to an inner recess 50 that is in communication with the transition slot 47. The outflow duct 4 from the diluting sample-extractor is connected to such nipple.

Through the side of the frame 40 opposite the inlet-connecting block 48, the frame rim has a transition slot 51 for discharge of dilute slurry from the viewing chamber. An outlet-connecting block 52 bolted to the side of the frame 40 adjacent to the outlet transition slot 51 has a nipple 53 connected by a passage to a cavity 54 that is in registration with the outlet transition slot 51. The joint between the block 52 and the frame 40 is sealed by an O-ring 52'.

The thickness of the viewing chamber between the windows 43 is sufficiently small, such as one-half inch, to pass light rays readily when the viewing chamber is filled with dilute slurry in which the fibers and foreign matter are suspended. The flow of dilute slurry into the viewing chamber through the nipple 49 is in a direction perpendicular to the direction of flow through the transition slot 47 and the viewing chamber so that the velocity energy will be dampened by impact with the inlet block 48 and changing direction at a right angle to produce smooth flow of the dilute slurry at a reduced velocity through the viewing chamber between windows 43.

In order to monitor the dilute slurry photographically in the viewing chamber, it is desirable to take periodic photographs at high speed. The exposure time for each photograph may be as fast as one ten-thousandth of a second, and several successive pictures can be taken each second. Also, the cross-sectional area of the passage for flow of the dilute slurry between the windows 43 and the ledges 42 is much greater than the cross section of the passage through the inlet nipple 49 so that the velocity of the flow through the viewing window is much less than the velocity of inflow through the inlet nipple. The flow velocity through the inlet nipple 49 may be as much as 10 feet per second, whereas the flow velocity through the viewing chamber between the ledges 42 and windows 43 may be slowed to approximately 6 inches per second.

I claim:

1. Apparatus for monitoring slurry flowing in a pressure pipe comprising a diluting sample-extractor adjacent to the pressure pipe and including an outflow duct, a sampling port opening from the pressure pipe to said extractor for flow of slurry from the pressure pipe into and through said outflow duct, a diluent supply conduit connected to said outflow duct by a connection to a side of said outflow duct and extending circumferentially over only a minor portion of the circumference of said outflow duct for producing an inflow stream of diluent to said flow of slurry flowing through said outflow duct in a direction transversely of the direction of flow of said flow of slurry flowing through said outflow duct and intersecting said flow of slurry for mixing with said flow of slurry, a second supply conduit for supplying diluent and connected to said extractor at a location adjacent to the entering side of said sampling port, and evaluation mechanism for evaluating the diluted slurry supplied by said outflow duct.

2. Apparatus for monitoring slurry flowing in a pressure pipe comprising a diluting sample-extractor adjacent to the pressure pipe and including an outflow duct, a sampling port opening from the pressure pipe to said extractor for flow of slurry from the pressure pipe into and through said outflow duct, a diluent supply conduit connected to said outflow duct by a connection to a side of said outflow duct and extending circumferentially over only a minor portion of the circumference of said outflow duct for producing an inflow stream of diluent to said flow of slurry flowing through said outflow duct in a direction transversely of the direction of flow of said flow of slurry flowing through said outflow duct and intersecting said flow of slurry for mixing with said flow of slurry; said sample-extractor including a casing that projects through the wall of the pressure pipe into the interior of such pressure pipe, said sampling port being spaced from the end of said casing, the portion of said casing projecting into the pressure pipe forming an annular flange encircling said sampling port, the connection of said diluent supply conduit to said outflow duct being located at the side of said sampling port opposite said flange, and a second supply conduit for supplying diluent and connected to said extractor at a location within said annular flange and adjacent to the entering side of said sampling port, and evaluation mechanism for evaluating the diluted slurry supplied by said outflow duct.

3. Apparatus for monitoring slurry flowing in a pressure pipe comprising a diluting sample-extractor adjacent to the pressure pipe and including an outflow duct, a sampling port opening from the pressure pipe to said extractor for flow of slurry from the pressure pipe into and through said outflow duct, a diluent supply conduit connected to said outflow duct by a connection to a side of said outflow duct and extending circumferentially over only a minor portion of the circumference of said outflow duct for producing an inflow stream of diluent to said flow of slurry flowing through said outflow duct in a direction transversely of the direction of flow of said flow of slurry flowing through said outflow duct and intersecting said flow of slurry for mixing with said flow of slurry, a portion of said diluent supply conduit extending substantially parallel to said outflow duct for flow of diluent therethrough in one direction and for flow of diluted slurry through said outflow duct in substantially the opposite direction, said diluent supply conduit and said outflow duct being separated by a common wall, means closing the end of said diluent supply conduit adjacent to the pressure pipe, a crossfeed port through said common wall adjacent to said diluent supply conduit end-closing means forming the connection connecting said diluent supply conduit to said outflow duct, and evaluation mechanism for evaluating the diluted slurry supplied by said outflow duct.

4. Apparatus for monitoring slurry flowing in a pressure pipe comprising a diluting sample-extractor adjacent to the pressure pipe and including an outflow duct, a sampling port opening from the pressure pipe to said extractor for flow of slurry from the pressure pipe into and through said outflow duct, a diluent supply conduit connected to said outflow duct by a connection to a side of said outflow duct and extending circumferentially over only a minor portion of the circumference of said outflow duct for producing an inflow stream of diluent to said flow of slurry flowing through said outflow duct in a direction transversely of the direction of flow of said flow of slurry flowing through said outflow duct and intersecting said flow of slurry for mixing with said flow of slurry, said supply conduit for the diluent forming an annular duct encircling said outflow duct and having a closed end between said sampling port and said connection of said diluent supply conduit to said outflow duct, and evaluation mechanism for evaluating the diluted slurry supplied by said outflow duct.

* * * * *